United States Patent
Choi et al.

(10) Patent No.: US 11,066,638 B2
(45) Date of Patent: Jul. 20, 2021

(54) METHOD OF PREPARING BACTERIAL GHOSTS FROM GRAM-POSITIVE BACTERIA BY HYDROCHLORIC ACID TREATMENT

(71) Applicant: PAICHAI UNIVERSITY INDUSTRY-ACADEMIC COOPERATION FOUNDATION, Daejeon (KR)

(72) Inventors: Chang Won Choi, Daejeon (KR); Seong Mi Ji, Incheon (KR); Hyun Jung Park, Cheongdo-gun (KR); Sung Oh, Daejeon (KR); Nagarajan Vinod, Daejeon (KR); Han Byul No, Daejeon (KR)

(73) Assignee: PAICHAI UNIVERSITY INDUSTRY-ACADEMIC COOPERATION FOUNDATION, Daejeon (KR)

( * ) Notice: Subject to any disclaimer, the term of this patent is extended or adjusted under 35 U.S.C. 154(b) by 29 days.

(21) Appl. No.: 15/549,325

(22) PCT Filed: Jul. 13, 2016

(86) PCT No.: PCT/KR2016/007591
§ 371 (c)(1),
(2) Date: Aug. 7, 2017

(87) PCT Pub. No.: WO2017/179766
PCT Pub. Date: Oct. 19, 2017

(65) Prior Publication Data
US 2018/0066225 A1 Mar. 8, 2018

(30) Foreign Application Priority Data

Apr. 15, 2016 (KR) ........................ 10-2016-0046466

(51) Int. Cl.
| | | |
|---|---|---|
| *C12N 1/20* | (2006.01) | |
| *C12N 1/06* | (2006.01) | |
| *A61K 39/02* | (2006.01) | |
| *A61K 39/07* | (2006.01) | |
| *A61K 39/085* | (2006.01) | |
| *A61K 39/05* | (2006.01) | |
| *A61K 39/08* | (2006.01) | |
| *A61K 39/09* | (2006.01) | |
| *A61K 39/00* | (2006.01) | |
| *A61K 47/69* | (2017.01) | |

(52) U.S. Cl.
CPC ............ *C12N 1/20* (2013.01); *A61K 39/0208* (2013.01); *A61K 39/05* (2013.01); *A61K 39/07* (2013.01); *A61K 39/08* (2013.01); *A61K 39/085* (2013.01); *A61K 39/092* (2013.01); *A61K 47/6901* (2017.08); *C12N 1/06* (2013.01); *A61K 39/00* (2013.01); *A61K 2039/521* (2013.01)

(58) Field of Classification Search
None
See application file for complete search history.

(56) References Cited

U.S. PATENT DOCUMENTS

| | | | | |
|---|---|---|---|---|
| 6,896,887 | B2 * | 5/2005 | Leenhouts | ........... C07K 14/335 |
| | | | | 424/234.1 |
| 7,968,323 | B2 | 6/2011 | Lubitz | |
| 2003/0186851 | A1 | 10/2003 | Leenhouts et al. | |

FOREIGN PATENT DOCUMENTS

| | | |
|---|---|---|
| KR | 1999-007306 A | 1/1999 |
| KR | 10-0273847 B1 | 12/2000 |
| KR | 10-2005-0028051 A | 3/2005 |
| KR | 10-2005-0053749 A | 6/2005 |
| KR | 10-0765357 B1 | 10/2007 |
| KR | 10-1101263 B1 | 1/2012 |
| KR | 10-1449628 B1 | 10/2014 |
| WO | WO-2014179754 A2 * | 11/2014 ............. A01N 33/12 |

OTHER PUBLICATIONS

Vinod, N. et al. 2015. Generation of a novel *Staphylococcus aureus* ghost vaccine and examination of its immunogenicity against virulent challenge in rats. Infection and Immunity 83(7): 2957-2965. specif. p. 2957.*

Jones, G.S. et al. 2013. Listeria monocytogenes: cultivation and laboratory maintenance. Current Protocols in Microbiology 31: 9B2.1-9B2.7.see NIH Public Access page numbering 1-9. specif. pp. 5, 6.*

Navarre, W.W. et al. 1999. Surface proteins of gram-positive bacteria and mechanisms of their targeting to the cell wall envelope. Microbiology and Molecular Biology Reviews 63(1): 174-229. specif. pp. 175-180.*

Haidinger et al., "Online Monitoring of *Escherichia coli* Ghost Production", Applied and Environmental Microbiology, 2003, vol. 69, No. 1, pp. 468-474.

(Continued)

*Primary Examiner* — Lynn Y Fan
*Assistant Examiner* — Sharon M. Papciak
(74) *Attorney, Agent, or Firm* — Knobbe Martens Olson & Bear LLP

(57) ABSTRACT

The present invention relates to bacterial ghosts, and more particularly, to a method of preparing bacterial ghosts from gram-positive bacteria by hydrochloric acid treatment. Specifically, according to the present invention, when gram-positive bacteria were cultured after being treated with a minimum inhibitory concentration (MIC) of hydrochloric acid capable of inhibiting colony formation of gram-positive bacteria, bacterial ghosts were effectively formed. Since the formed bacterial ghosts have no intracellular proteins or DNA while preserving cell wall integrity, the risk of side effects such as secondary infection caused by bacterial growth when the bacterial ghosts are administered to humans is low. Therefore, the bacterial ghosts prepared from gram-positive bacteria according to the method of the present invention may be effectively used as a vaccine or a foreign antigen carrier for preventing or treating gram-positive bacterial infection.

1 Claim, 7 Drawing Sheets

(56) References Cited

OTHER PUBLICATIONS

Ebensen et al., "Bacterial Ghosts are an Efficient Delivery System for DNA Vaccines", The Journal of Immunology, 2004, vol. 172, pp. 6858-6865.
Konopa et al., "Isolation of Coliphage Lambda Ghosts Able to Absorb Onto Bacterial Cells", Biochimica et Biophysic Acta, 1975, vol. 399, pp. 460-467.
Amara et al., "Sponge-Like: A New Protocol for Preparing Bacterial Ghosts", The Scientific World Journal, vol. 2013, Article ID 545741 in 7 pages.
Vinod et al., "Chemically induced *Salmonella enteritidis* Ghosts as a Novel Vaccine Candidate Against Virulent Challenge in a Rat Model", Vaccine, 2014, vol. 32, pp. 3249-3255.
Vinod et al., "Generation of a Novel *Staphylococcus aureus* Ghost Vaccine and Examination of Its Immunogenicity against Virulent Challenge in Rats", Infection and Immunity, 2015, vol. 83, No. 7, pp. 2957-2965.

\* cited by examiner

METHOD OF PREPARING BACTERIAL GHOSTS FROM GRAM-POSITIVE BACTERIA BY HYDROCHLORIC ACID TREATMENT

CROSS-REFERENCE TO RELATED APPLICATION

This application claims priority to and the benefit of Korean Patent Application No. 10-2016-0046466, filed on Apr. 15, 2016, the disclosure of which is incorporated herein by reference in its entirety.

BACKGROUND

1. Field of the Invention

The present invention relates to bacterial ghosts, and more particularly, to a method of preparing bacterial ghosts from gram-positive bacteria by hydrochloric acid treatment.

2. Discussion of Related Art

A bacterial ghost is simply defined as a structure in which the intracellular components (cytoplasmic contents) of a microorganism are removed and the interior thereof is empty, while the cell membrane of the microorganism is completely maintained in an envelope form. A bacterial ghost is not considered a genetically modified organism (GMO) because the bacterial ghost is virtually a dead cell lacking intracellular DNA or genetic materials.

However, since bacterial ghosts retain the envelope form of live bacteria and antigenic determinants present on the envelope, bacterial ghosts may exhibit functional effects similar to live vaccines. In particular, when treating bacterial infections, since vaccines (ghost vaccines) using bacterial ghosts do not have an inhibitory effect on immune induction, which may be caused by a large amount of nonspecific cytoplasmic substances, vaccines may easily stimulate innate and adaptive immune systems without addition of foreign adjuvants. In addition to these advantage, the vaccines using bacterial ghosts are inexpensive. Thus, ghost vaccines have been recognized as an alternative to effectively overcome the limitations of conventional chemical vaccines.

In addition, since bacterial ghosts do not have the ability to multiply and are not pathogenic unlike live bacteria, i.e., they are inactivated, the bacterial ghosts may be attached to animal, human or plant specific tissues or cells. In addition, since bacterial ghosts may be introduced into plant cells or animal cells, they may be used as a delivery system capable of effectively transferring recombinant antigens or nucleic acids to target cells.

Various methods of preparing such bacterial ghosts have been developed. The most common method of preparing bacterial ghosts is E protein-mediated lysis, which involves transforming gram-negative bacteria with a cloned plasmid containing bacteriophage φX174 lysis gene E and expressing the gene. According to the method, the expression of gene E is suppressed in the transformed bacteria, and the E protein is expressed by gene E depending on temperature change. The synthesized E protein does not cause physicochemical damage to the surface structure of bacteria, but forms transmembrane tunnels in bacterial membranes and cell walls, ultimately releasing cell constituents (Non-Patent Document 1). In this method, when a plasmid is cloned, various genes can be selected so that a desired protein is expressed as an antigen, and mass production can be carried out by conventional transformation techniques and culture methods.

However, in the case of methods of preparing bacterial ghosts by transformation of a cloned plasmid, including the E protein-mediated lysis method, these methods are disadvantageous in that they require molecular biological techniques which require a multistage process, and are accompanied by high cost and a long manufacturing time. Therefore, there is a demand for a mass production method of bacterial ghosts, which requires a simple manufacturing technique and a low production cost and can save time.

Recently, a method of preparing bacterial ghosts using a chemical substance such as SDS, sodium hydroxide (NaOH) or hydrogen peroxide ($H_2O_2$) using *E. coli* BL21 (DE3) pLysS, a gram-negative bacterium, as a model has been reported (Non-Patent Document 4). In addition, a method of preparing bacterial ghosts by treating *E. coli* DH5α with a minimum inhibitory concentration (MIC) of ammonium sulfate (($NH_4)_2SO_4$), calcium chloride ($CaCl_2$) or ethylenediaminetetraacetic acid (EDTA) to affect cell walls has been reported (Patent Document 4).

Most reported bacterial ghosts and vaccines using the same are modeled on gram-negative bacteria, such as *Escherichia coli* or *salmonella*. As a method of preparing bacterial ghosts, to which gram-positive bacteria are applied, a method of preparing bacterial ghosts by treating *Salmonella enterica*, a gram-negative bacterium, and *Staphylococcus aureus*, a gram-positive bacterium, with basic sodium hydroxide has been reported. According to the method, it was confirmed that, when experimental animals were immunized with bacterial ghosts prepared from *Salmonella* or *Staphylococcus*, immunity was induced, suggesting that the bacterial ghosts may be used as a vaccine (Non-Patent Document 5 and Non-Patent Document 6).

However, an effect as a vaccine may be reduced in the case of bacterial ghosts prepared by treatment with basic sodium hydroxide because proteins in the cell membrane, acting as antigenic determinants, may be released by bases depending on the type of protein. To overcome this problem, research on a method of preparing bacterial ghosts in an acidic environment is required, but research and patents on bacterial ghosts using acids have not been reported.

Accordingly, the present inventors have made efforts to develop a method of preparing bacterial ghosts from gram-positive bacteria using an acid. As a result, a minimum inhibitory concentration (MIC) of hydrochloric acid capable of inhibiting colony formation of *Listeria monocytogenes*, a gram-positive bacterium, was determined. In addition, when *Listeria monocytogenes* was cultured after being treated with the MIC of hydrochloric acid, bacterial ghosts were effectively formed. Finally, it was confirmed that the bacterial ghosts prepared from *Listeria*, gram-positive bacteria, according to the present invention may be usefully used as a vaccine or a foreign antigen carrier for preventing or treating gram-positive bacterial infection. Thus, the present invention was completed.

PRIOR ART DOCUMENT

Patent Document (Patent Document 1) KR 10-0273847 B1 (2000 Dec. 15)
(Patent Document 2) KR 10-0765357 B1 (2007 Oct. 10)

(Patent Document 3) US 7968323 B2 (2011 Jun. 28)
(Patent Document 4) KR 10-1449628 B1 (2014 Oct. 2)

Non-Patent Document (Non-Patent Document 1) Haidinger, W., et al. Applied and Environmental Microbiology 69.1 (2003): 468-474.
(Non-Patent Document 2) Ebensen, Thomas, et al. The Journal of Immunology 172.11 (2004): 6858-6865.
(Non-Patent Document 3) Konopa, Grazyna, and Karol Taylor. Biochimica et Biophysica Acta (BBA)-General Subjects 399.2 (1975): 460-467.
(Non-Patent Document 4) Amara, Amro A., Mounir M. Salem-Bekhit, and Fars K. Alanazi. The Scientific World Journal 2013 (2013).
(Non-Patent Document 5) Vinod, Nagarajan, et al. Vaccine 32.26 (2014): 3249-3255.
(Non-Patent Document 6) Vinod, Nagarajan, et al. Infection and Immunity 83.7 (2015): 2957-2965.

SUMMARY OF THE INVENTION

Accordingly, the present inventors prepared bacterial ghosts from *Listeria monocytogenes* by treating *Listeria monocytogenes* with hydrochloric acid, and thus the present invention was completed.

Therefore, the present invention has been made in view of the above problems, and it is an objective of the present invention to provide a method of preparing bacterial ghosts from gram-positive bacteria.

It is another objective of the present invention to provide bacterial ghosts prepared from gram-positive bacteria according to the method.

It is still another objective of the present invention to provide a use of bacterial ghosts prepared from gram-positive bacteria according to the method.

It is yet another objective of the present invention to provide a vaccine composition for preventing and treating gram-positive bacterial infection, including the bacterial ghosts prepared from gram-positive bacteria as an active ingredient.

It is yet another objective of the present invention to provide a method of preventing or treating gram-positive bacterial infection, including a step of administering the bacterial ghosts prepared from gram-positive bacteria to an individual in need of treatment.

It is yet another objective of the present invention to provide a use of a vaccine composition for preventing and treating gram-positive bacterial infection, the vaccine composition including the bacterial ghosts prepared from gram-positive bacteria as an active ingredient.

In accordance with the present invention, the above and other objectives can be accomplished by the provision of a method of preparing bacterial ghosts from gram-positive bacteria, including
a step of inoculating a medium with gram-positive bacteria, followed by culturing;
a step of obtaining the gram-positive bacteria from the culture medium cultured in the step of inoculating;
a step of treating the gram-positive bacteria obtained in the step of obtaining with hydrochloric acid to form bacterial ghosts; and
a step of obtaining the bacterial ghosts formed in the step of treating.

According to an embodiment of the present invention, the gram-positive bacteria in the step of inoculating may be any one or more selected from the group consisting of *Listeria, Staphylococcus aureus, Streptococcus pneumoniae, Bacillus anthracis, Corynebacterium diphtherias* and *Clostridium tetani*.

According to an embodiment of the present invention, the treatment in the step of treating may be treatment with hydrochloric acid at a minimum inhibitory concentration (MIC).

According to an embodiment of the present invention, the minimum inhibitory concentration of hydrochloric acid may be 6.25 mg/ml.

According to an embodiment of the present invention, the treatment in the step of treating may be performed with hydrochloric acid for 10 to 60 minutes.

According to an embodiment of the present invention, the treatment in the step of treating may be performed with hydrochloric acid at 30 to 40° C.

In accordance with an aspect of the present invention, the above and other objectives can be accomplished by the provision of bacterial ghosts prepared from gram-positive bacteria according to the method.

In accordance with another aspect of the present invention, there is provided a use of bacterial ghosts prepared from gram-positive bacteria according to the method.

In accordance with still another aspect of the present invention, there is provided a vaccine composition for preventing and treating gram-positive bacterial infection, including the bacterial ghosts prepared from gram-positive bacteria as an active ingredient.

In accordance with yet another aspect of the present invention, there is provided a method of preventing or treating gram-positive bacterial infection, including a step of administering the bacterial ghosts prepared from gram-positive bacteria to an individual in need of treatment.

In accordance with yet another aspect of the present invention, there is provided a use of a vaccine composition for preventing and treating gram-positive bacterial infection, the vaccine composition including the bacterial ghosts prepared from gram-positive bacteria as an active ingredient.

According to a preferred embodiment of the present invention, the gram-positive bacteria may be any one or more selected from the group consisting of *Listeria, Staphylococcus aureus, Streptococcus pneumoniae, Bacillus anthracis, Corynebacterium diphtherias* and *Clostridium tetani*.

According to a preferred embodiment of the present invention, the vaccine composition may include bacterial ghosts as an inactivated vaccine or as a foreign antigen carrier.

As apparent from the above description, the present invention provides bacterial ghosts prepared from gram-positive bacteria by treatment with hydrochloric acid and a method of preparing the same.

According to the present invention, when gram-positive bacteria are cultured after being treated with a minimum inhibitory concentration (MIC) of hydrochloric acid capable of inhibiting colony formation of gram-positive bacteria, bacterial ghosts can be effectively formed. In addition, since the formed bacterial ghosts have no intracellular proteins or DNA while preserving cell wall integrity, the risk of side effects such as secondary infection caused by bacterial growth when the bacterial ghosts are administered to humans is low. Therefore, the bacterial ghosts prepared from gram-positive bacteria according to the method of the present invention can be effectively used as a vaccine or a foreign antigen carrier for preventing or treating gram-positive bacterial infection.

BRIEF DESCRIPTION OF THE DRAWINGS

The above and other objects, features and advantages of the present invention will become more apparent to those of ordinary skill in the art by describing in detail embodiments thereof with reference to the accompanying drawings, in which.

DETAILED DESCRIPTION OF EMBODIMENTS

Figure 1:
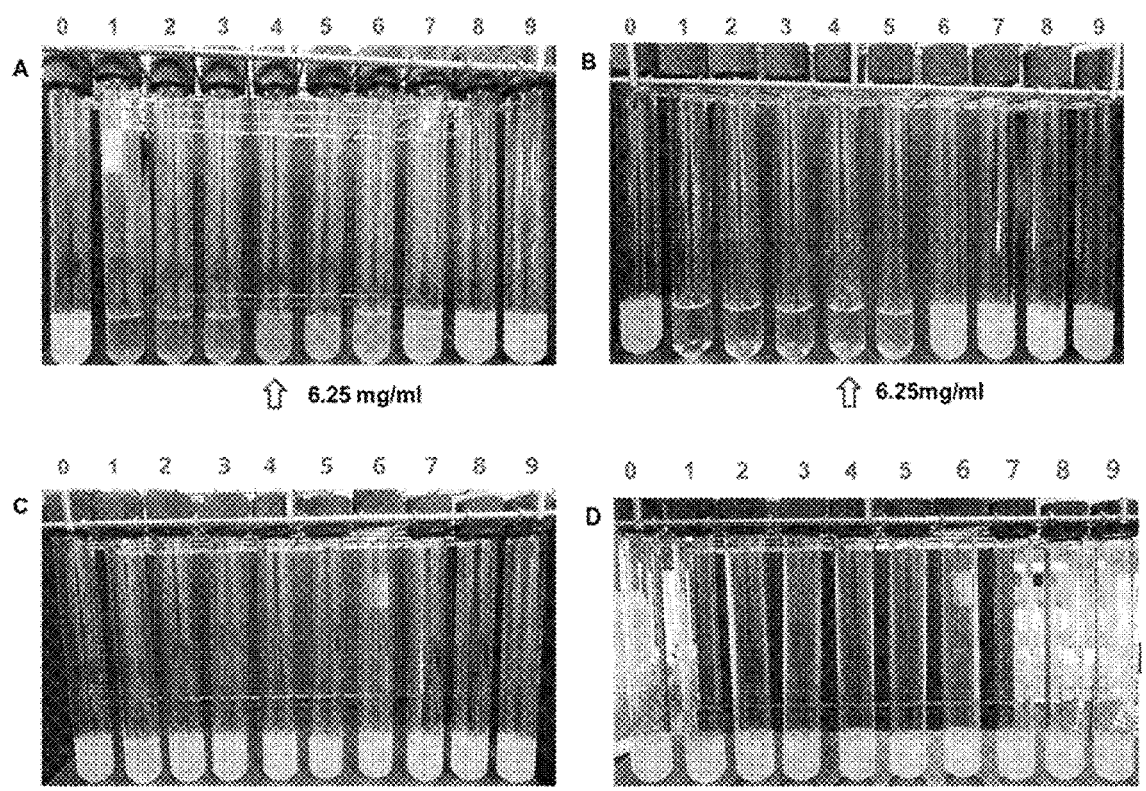
FIG. 1 shows the results of a culture experiment conducted to determine the minimum inhibitory concentration (MIC) of hydrochloric acid in a BHI liquid medium for preparation of bacterial ghosts using *Listeria monocytogenes*.

Hereinafter, the present invention is described in more detail.

As described above, in the conventional method of preparing bacterial ghosts by chemical treatment, bacterial ghosts are prepared from gram-positive bacteria by treatment with basic sodium hydroxide. However, there has been no research on a method of preparing bacterial ghosts from gram-positive bacteria by treating with acids.

According to the present invention, when gram-positive bacteria were cultured after being treated with a minimum inhibitory concentration (MIC) of hydrochloric acid capable of inhibiting colony formation of gram-positive bacteria, bacterial ghosts were effectively formed. Since the formed bacterial ghosts have no intracellular proteins or DNA while preserving cell wall integrity, the risk of side effects such as secondary infection caused by bacterial growth when the bacterial ghosts are administered to humans is low. Therefore, the bacterial ghosts prepared from gram-positive bacteria according to the method of the present invention may be effectively used as a vaccine or a foreign antigen carrier for preventing or treating gram-positive bacterial infection.

Accordingly, the present invention provides a method of preparing bacterial ghosts from gram-positive bacteria, including a step of inoculating a medium with gram-positive bacteria, followed by culturing;

a step of obtaining the gram-positive bacteria from the culture medium cultured in the step of inoculating;

a step of treating the gram-positive bacteria obtained in the step of obtaining with hydrochloric acid to form bacterial ghosts; and a step of obtaining the bacterial ghosts formed in the step of treating.

In the step of inoculating according to the present invention, gram-positive bacteria are preferably any one or more selected from the group consisting of *Listeria, Staphylococcus aureus, Streptococcus pneumoniae, Bacillus anthracis, Corynebacterium diphtherias* and *Clostridium tetani*, without being limited thereto, and may be any gram-positive bacteria, which are known as pathogenic bacteria in the art and may be used as an inactivated vaccine or a foreign antigen carrier.

Specifically, *Listeria* is more preferably *Listeria monocytogenes, Listeria denitrificans* (*L. denitrificans*), *Listeria grayi* (*L. grayi*) or *Listeria murrayi* (*L. murrayi*). More specifically, *Listeria* is most preferably *Listeria monocytogenes*, without being limited thereto, because *Listeria monocytogenes* is known to be pathogenic among *Listeria*.

In the step of inoculating according to the present invention, the culture of gram-positive bacteria is preferably performed at 30 to 40° C., more preferably at 37° C. In addition, the culture of gram-positive bacteria is preferably performed for 65 to 75 hours, more preferably for 72 hours. During culturing of the gram-positive bacteria, the cell walls of cells in the exponential growth phase of bacterial growth are susceptible to hydrochloric acid. In contrast, cells in the stationary phase after the exponential growth phase have elastic cell walls, and the degree of damage to envelopes by the MIC of hydrochloric acid is not large. Therefore, lysis tunnel structures may be effectively formed.

In the step of treating, the treatment is preferably performed with the minimum inhibitory concentration (MIC) of hydrochloric acid, without being limited thereto. Specifically, the minimum inhibitory concentration of hydrochloric acid is preferably 6 to 7 mg/ml, more preferably 6.25 mg/ml. In the method of preparing bacterial ghosts from gram-positive bacteria according to the present invention, it is important to treat with hydrochloric acid at a minimum inhibitory concentration. When hydrochloric acid is treated at less than the MIC of hydrochloric acid, bacteria may survive because of incomplete lysis of gram-positive bacteria. Thus, the prepared bacterial ghosts may not be used as an inactivated vaccine or a foreign antigen carrier. In addition, when hydrochloric acid is treated at more than the MIC of hydrochloric acid, the degree of damage to the envelope structure of gram-positive bacteria is increased, and complete tunnel structures may not be formed in the cell membrane. As a result, a perfect type of bacterial ghost may not be produced, and an effect as an inactivated vaccine or a foreign antigen may be reduced.

In the step of treating, the treatment is preferably performed with hydrochloric acid for 10 to 60 minutes, more preferably for 15 to 60 minutes, without being limited thereto. According to the method of preparing bacterial ghosts from gram-positive bacteria of the present invention, at about 15 minutes after the MIC of hydrochloric acid has been applied, the lysis rate of gram-positive bacteria may be 100%. However, when bacterial ghosts are used as a vaccine, the hydrochloric acid treatment is preferably performed for 60 minutes in consideration of safety.

In the step of treating, the treatment is preferably performed with hydrochloric acid at 30 to 40° C., more preferably at 37° C., without being limited thereto. When the treatment is performed at a temperature of 30° C. or lower or 40° C. or higher, the MIC of hydrochloric acid may be varied, and the production efficiency of the bacterial ghosts of the present invention may be varied.

In a specific embodiment of the present invention, the MIC of hydrochloric acid for preparing bacterial ghosts from *Listeria monocytogenes* was determined. When *Listeria monocytogenes* was treated with hydrochloric acid at a concentration of 6.25 mg/ml, *Listeria* growth was effectively inhibited. Thus, the concentration was determined as the MIC of hydrochloric acid. In addition, it was confirmed that the degree of growth of live cells was effectively inhibited at the MIC (FIGS. 1A and 2). The MIC of sodium hydroxide used as a control was 6.25 mg/ml. In the case of ammonium sulfate or calcium chloride, which is known to be used to prepare bacterial ghosts from gram-negative bacteria, an inhibitory effect on bacterial growth was not observed even when bacteria were treated with ammonium sulfate or calcium chloride at a concentration of 500 mg/ml (FIGS. 1B to 1D).

Figure 3:
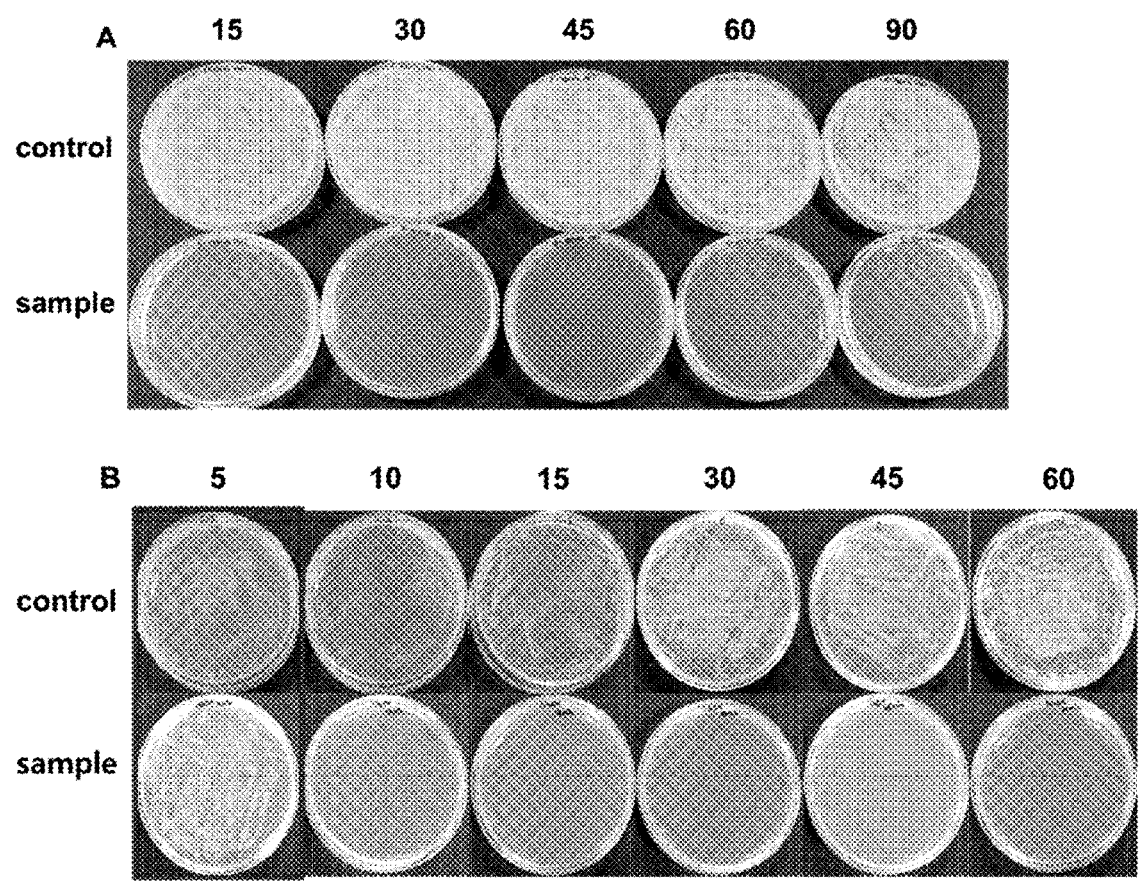
FIG. 3 shows the time course of formation of bacterial ghosts from *Listeria monocytogenes* after treatment with the MIC of hydrochloric acid or sodium hydroxide.

In addition, in preparation of bacterial ghosts from *Listeria*, the optimum conditions for treating with the MIC of hydrochloric acid were determined. As a result, when *Listeria* were treated with the MIC of hydrochloric acid for about 15 minutes, bacterial ghosts were effectively formed (FIG. 3).

Figure 4:
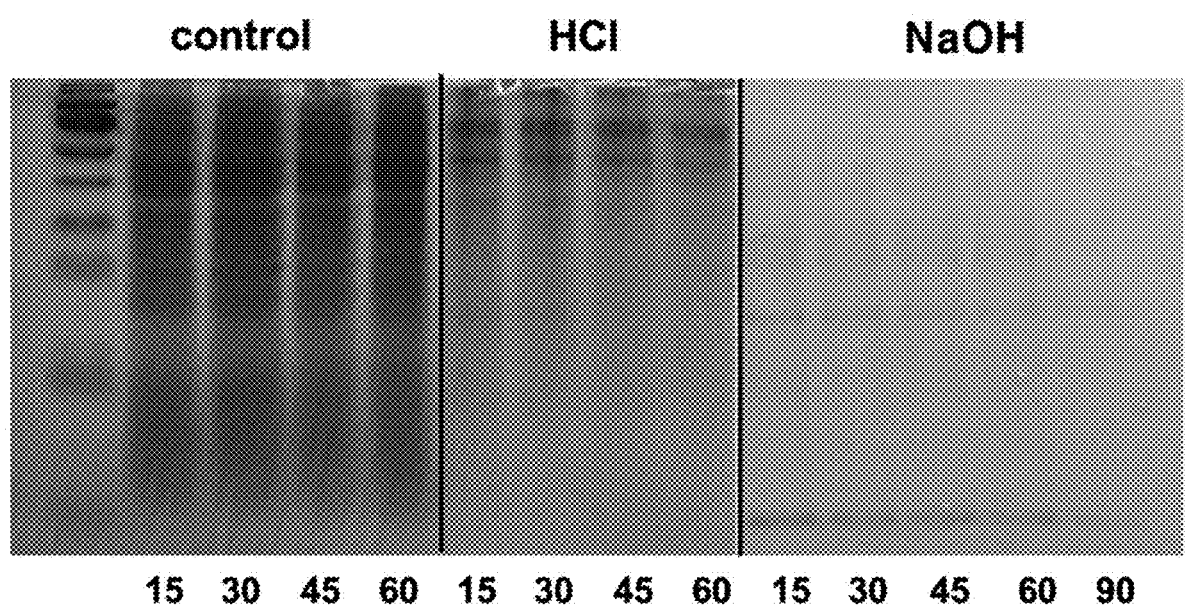
FIG. 4 shows the results of SDS-PAGE showing the total amount of proteins remaining in the bacterial ghosts of *Listeria monocytogenes* over time after treatment with the MIC of hydrochloric acid or sodium hydroxide.
Figure 5:
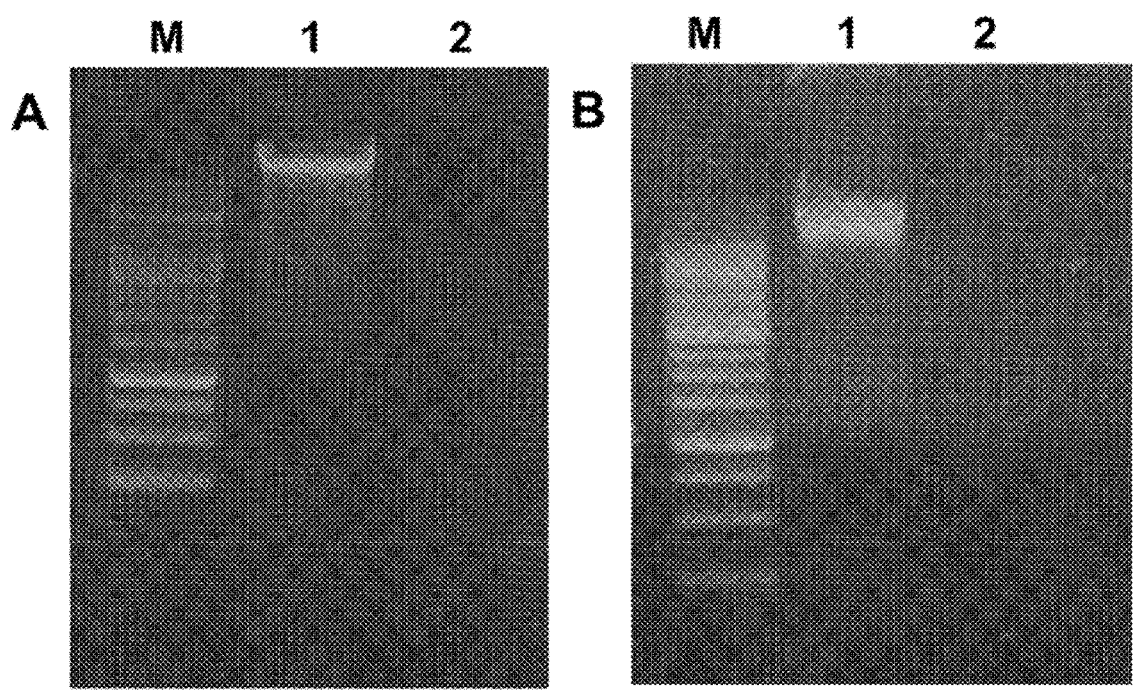
FIG. 5 shows the results (images A and B) of agarose gel electrophoresis for confirming the presence of genomic DNA remaining in the bacterial ghosts of *Listeria monocytogenes* after treatment with the MIC of hydrochloric acid or sodium hydroxide.
Figure 6:
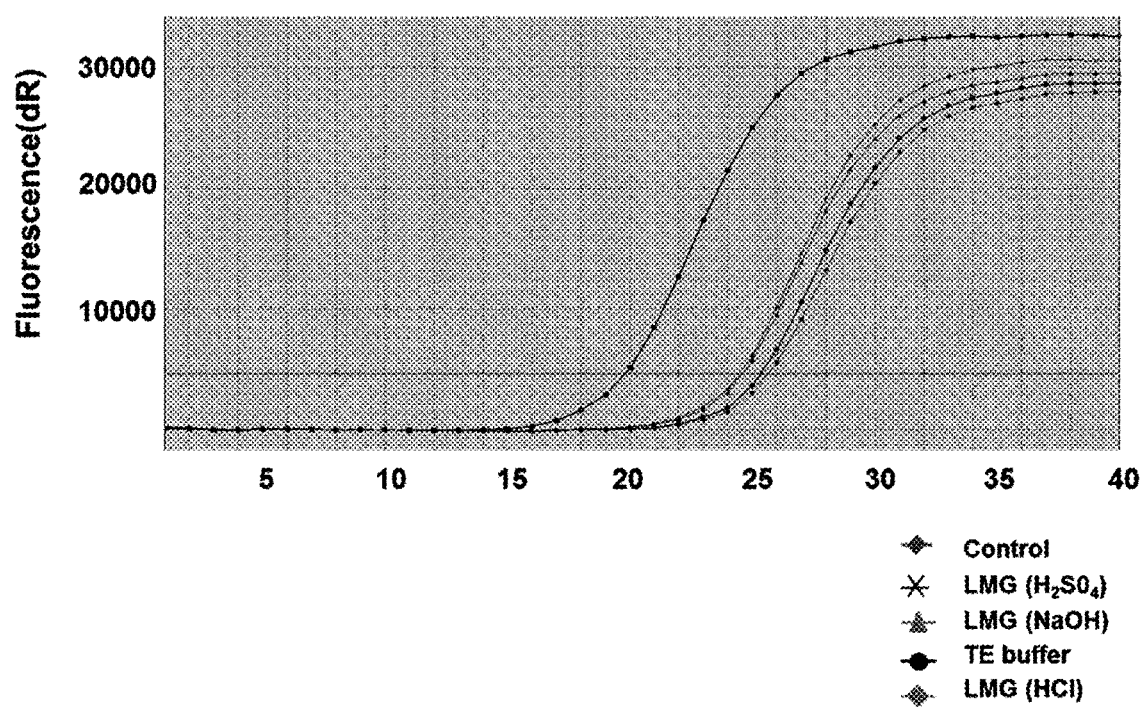
FIG. 6 shows the result of real-time PCR analysis for confirming the presence of genomic DNA remaining in the bacterial ghosts of *Listeria monocytogenes* after treatment with the MIC of hydrochloric acid or sodium hydroxide.

In addition, it was confirmed that bacterial ghosts prepared from *Listeria* according to the method of the present invention may be effectively used. Lysed tunnels were effectively formed in the cell walls of the bacterial ghosts, no protein and genomic DNA remained in the cytoplasm, and only cell wall proteins for retaining the structure of the bacterial ghosts were present (FIGS. 4 and 5). On the other hand, in the case of bacterial ghosts prepared by treating with sodium hydroxide under the same conditions, trace amounts of genomic DNA remained in the cytoplasm (FIG. 6). Based on these results, it was confirmed that the method using hydrochloric acid treatment was more effective.

Figure 7:
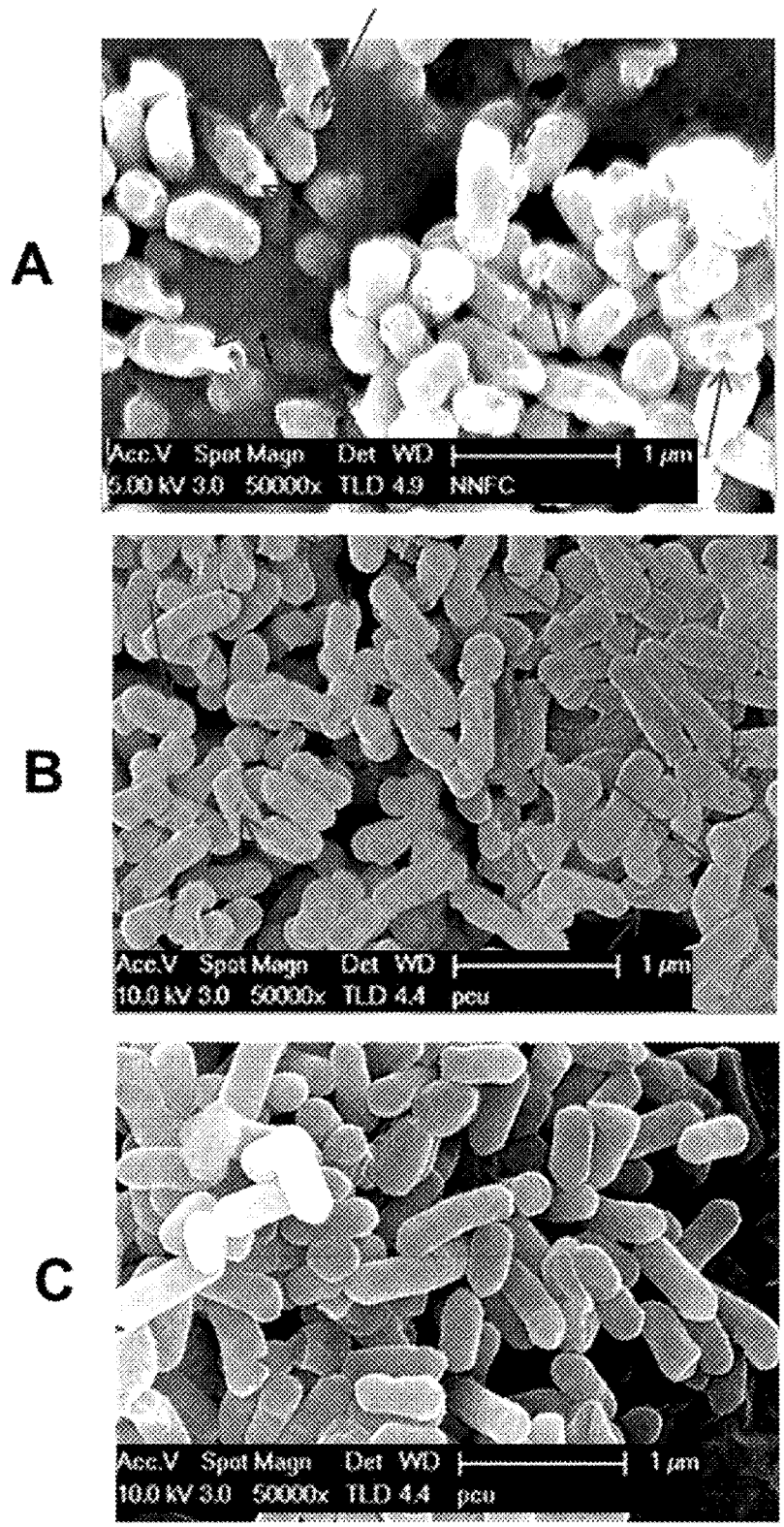
FIG. 7 shows the results (images A, B and C) of scanning electron microscope (SEM) analysis for observing the surface morphology of the bacterial ghosts of *Listeria monocytogenes* after treatment with the MIC of hydrochloric acid or sodium hydroxide.

In addition, the surface of bacterial ghosts prepared from *Listeria* by treatment with hydrochloric acid or sodium hydroxide was analyzed. As a result, lysis tunnel structures were formed in bacterial ghosts treated with hydrochloric acid, and a slightly lysed envelope shape was observed (FIG. 7).

Accordingly, according to the present invention, when gram-positive bacteria were cultured after being treated with a minimum inhibitory concentration (MIC) of hydrochloric acid capable of inhibiting colony formation of gram-positive bacteria, bacterial ghosts were effectively formed. Since the formed bacterial ghosts have no intracellular proteins or DNA while preserving cell wall integrity, the risk of side effects such as secondary infection caused by bacterial growth when the bacterial ghosts are administered to humans is low. Therefore, the bacterial ghosts prepared from gram-positive bacteria according to the method of the present invention may be effectively used as a vaccine or a foreign antigen carrier for preventing or treating gram-positive bacterial infection.

In addition, the present invention provides bacterial ghosts prepared from gram-positive bacteria according to the method of preparing bacterial ghosts from gram-positive bacteria of the present invention.

In addition, the present invention provides a use of the bacterial ghosts of gram-positive bacteria, which are prepared according to the method of preparing bacterial ghosts from gram-positive bacteria of the present invention.

In addition, the present invention provides a vaccine composition for preventing and treating gram-positive bacterial infection, including the bacterial ghosts prepared from gram-positive bacteria as an active ingredient.

In addition, the present invention provides a method of preventing or treating gram-positive bacterial infection, including a step of administering the bacterial ghosts prepared from gram-positive bacteria to an individual in need of treatment.

In addition, the present invention provides a use of a vaccine composition for preventing and treating gram-positive bacterial infection, the vaccine composition including the bacterial ghosts prepared from gram-positive bacteria as an active ingredient.

In the present invention, gram-positive bacteria are preferably any one or more selected from the group consisting of *Listeria, Staphylococcus aureus, Streptococcus pneumoniae, Bacillus anthracis, Corynebacterium diphtherias* and *Clostridium tetani*, without being limited thereto, and may be any gram-positive bacteria, which are known as pathogenic bacteria in the art and may be used as an inactivated vaccine or a foreign antigen carrier.

Specifically, *Listeria* is more preferably *Listeria monocytogenes, Listeria denitrificans* (*L. denitrificans*), *Listeria grayi* (*L. grayi*) or *Listeria murrayi* (*L. murrayi*). More specifically, *Listeria* is most preferably *Listeria monocytogenes*, without being limited thereto, because *Listeria monocytogenes* is known to be pathogenic among *Listeria*.

The vaccine composition of the present invention preferably contains the bacterial ghosts of gram-positive bacteria of the present invention as an inactivated vaccine or a foreign antigen carrier, without being limited thereto.

According to the present invention, when gram-positive bacteria were cultured after being treated with a minimum inhibitory concentration (MIC) of hydrochloric acid capable of inhibiting colony formation of gram-positive bacteria, bacterial ghosts were effectively formed. Since the formed bacterial ghosts have no intracellular proteins or DNA while preserving cell wall integrity, the risk of side effects such as secondary infection caused by bacterial growth when the bacterial ghosts are administered to humans is low. Therefore, the bacterial ghosts prepared from gram-positive bacteria according to the method of the present invention may be effectively used as a vaccine or a foreign antigen carrier for preventing or treating gram-positive bacterial infection.

Hereinafter, the present invention will be described in more detail with reference to examples. It will be apparent to those skilled in the art that these embodiments are for illustrative purposes only and that the scope of the present invention is not construed as being limited by these examples.

EXAMPLE 1

Preparation of Bacterial Ghosts Using *Listeria Monocytogenes*

<1-1> Identification of Minimum Inhibitory Concentration (MIC) for Preparation of Bacterial Ghosts In the present invention, the MIC of hydrochloric acid required for preparing bacterial ghosts from *Listeria monocytogenes* bacteria was identified.

Specifically, *Listeria monocytogenes*, a gram-positive bacterium, was cultured in a brain-heart infusion (BHI) medium at 7° C. and 200 rpm under shaking conditions overnight, and then the degree of bacterial growth was determined by measuring optical density at 600 nm using a Biochrom Libra S22 spectrophotometer. Next, hydrochloric acid was stepwise diluted with a fresh BHI medium to the concentrations shown in Table 1, and the cultured *Listeria monocytogenes* bacteria were inoculated at a concentration of $10^6$ CFU/ml, followed by incubation at 37° C. for 18 hours. After incubation, *Listeria monocytogenes* bacteria growth depending on the concentrations of hydrochloric acid was determined by measuring optical density at 600 nm. As positive control groups, ammonium sulfate, calcium chloride and sodium hydroxide reported in conventional methods of preparing bacterial ghosts were added to a BHI medium at concentrations shown in Table 1, respectively. Using a BHI medium not containing hydrochloric acid as a non-treated control group, *Listeria monocytogenes* bacteria growth was measured in the same manner as described above.

TABLE 1

Various concentrations of media used to identify MIC applied to prepare bacterial ghosts from *Listeria monocytogenes* bacteria

| Test tube No. | Treatment concentrations of chemical agents (mg/ml) | | | |
|---|---|---|---|---|
| | Hydrochloric acid HCl | Sodium hydroxide NaOH | Ammonium sulfate $(NH_4)_2SO_4$ | Calcium chloride $CaCl_2$ |
| 0 (Non-treated control groups) | — | — | — | — |
| 1 | 50 | 50 | 500 | 500 |
| 2 | 25 | 25 | 250 | 250 |
| 3 | 12.5 | 12.5 | 125 | 125 |
| 4 | 6.25 | 6.25 | 62.5 | 62.5 |
| 5 | 3.125 | 3.125 | 31.25 | 31.25 |
| 6 | 1.5625 | 1.5625 | 15.625 | 15.625 |
| 7 | 0.78125 | 0.78125 | 7.8125 | 7.8125 |
| 8 | 0.390625 | 0.390625 | 3.90625 | 3.90625 |
| 9 | 0.1953125 | 0.1953125 | 1.953125 | 1.953125 |

Figure 2:
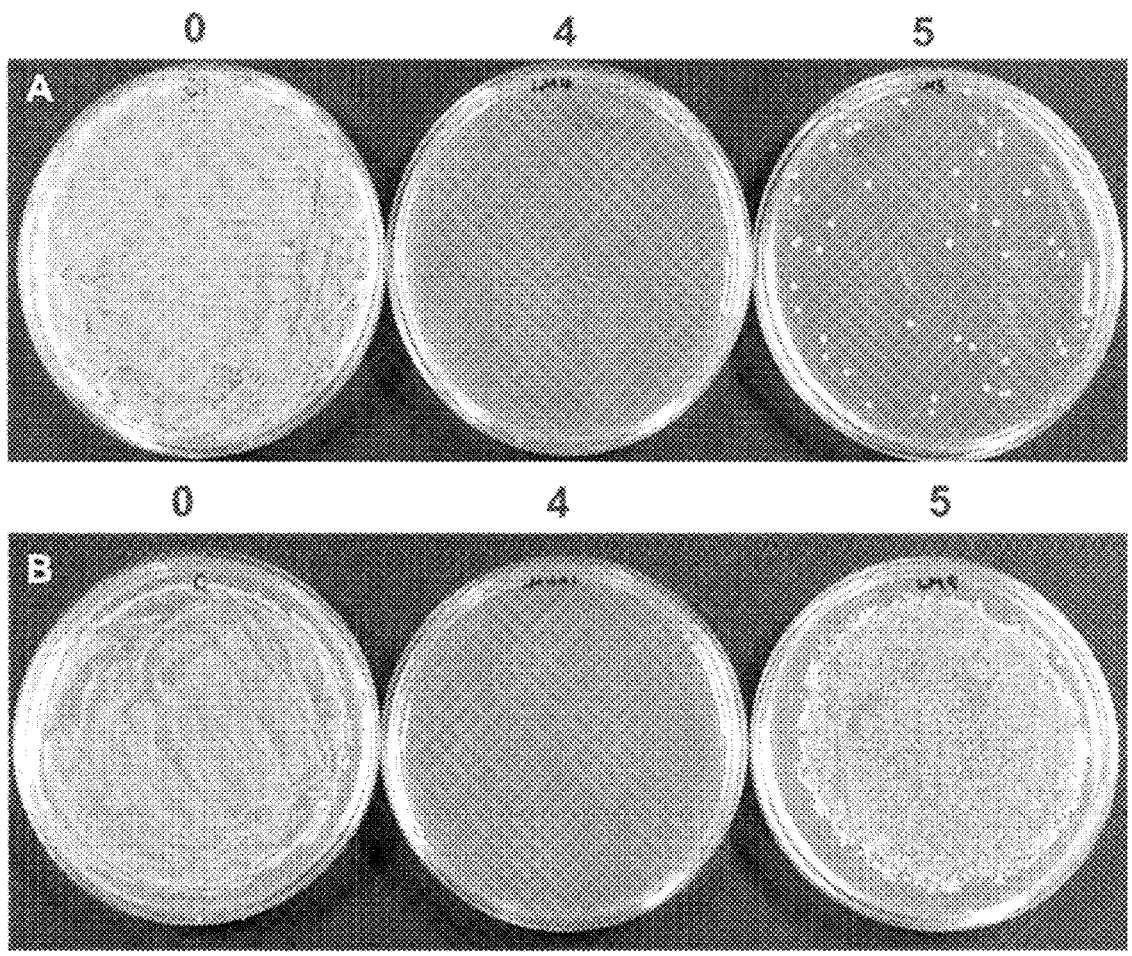
FIG. 2 shows the result of confirming the viability of bacteria when the bacteria were treated with various concentrations of hydrochloric acid or sodium hydroxide. The viability was determined by the presence or absence of colony formation on a BHI agar medium.

As a result, as shown in FIG. 1, when hydrochloric acid or sodium hydroxide was added to a BHI liquid medium at a concentration of 6.25 mg/ml, the pH of the medium was 3.16 or 10.75, respectively, and each medium effectively suppressed *Listeria* growth. Thus, the MICs of hydrochloric acid and sodium hydroxide for *Listeria* were determined to be 6.25 mg/ml (FIGS. 1A and 1B). On the other hand, in the case of ammonium sulfate and calcium chloride, previously used to prepare bacterial ghosts by effectively inhibiting the growth of *Escherichia coli*, a gram-negative bacterium, a growth inhibitory effect on *Listeria*, a gram-positive bacterium, was observed at a concentration of 500 mg/ml (FIGS. 1C and 1D).

<1-2> Determination of Cell Growth Capacity of bacterial Ghosts Prepared from *Listeria*

After the MICs of hydrochloric acid and sodium hydroxide for *Listeria*, a gram-positive bacterium, were determined, the degree of cell growth of bacterial ghosts prepared in a medium containing an MIC of hydrochloric acid or sodium hydroxide was then determined by a standard plating method.

Specifically, the *Listeria* cultured in Example <1-1> was plated onto BHI agar media at concentrations indicated in Table 2 below, incubated at 37° C. for 18 hours to induce colony formation, and then observed.

TABLE 2

Concentrations of bacteria, with which an agar medium was inoculated, to determine cell growth capacity of bacterial ghosts

| Test tube No. | Hydrochloric acid-treated groups | | Sodium hydroxide-treated groups | |
|---|---|---|---|---|
| | Hydrochloric acid concentrations (mg/ml) | Dilution factors of bacteria | Sodium hydroxide concentrations (mg/ml) | Dilution factors of bacteria |
| 0 | — | $10^{-3}$ | — | $10^{-3}$ |
| 4 | 6.25 | $10^0$ | 6.25 | $10^0$ |
| 5 | 3.125 | $10^{-1}$ | 3.125 | $10^0$ |

As a result, as shown in FIG. 2, in the case of hydrochloric acid treatment, when a non-treated control group was diluted to a dilution factor of 1/1000 and plated on a medium, a large number of colonies were formed on the medium. In addition, when a group treated with 3.125 mg/ml of hydrochloric acid was diluted to a dilution factor of 1/10 and plated on a medium, tens of colonies were also formed. In contrast, when a group treated with 6.25 mg/ml of hydrochloric acid, i.e., the MIC of hydrochloric acid, was plated on a medium without dilution, no viable colony was formed (FIG. 2A). In addition, in the case of sodium hydroxide treatment, when a non-treated control group was diluted to a dilution factor of 1/1000 and plated on a medium, numerous colonies were formed in the medium. When a group treated with 3.125 mg/ml of sodium hydroxide was plated without dilution, thousands of colonies were formed. In contrast, when a group treated with 6.25 mg/ml of sodium hydroxide, i.e., the MIC of sodium hydroxide, was plated without dilution, no viable colony was formed (FIG. 2B).

<1-3> Determining Optimal Time for Preparing Bacterial Ghosts from *Listeria*

After the MICs of hydrochloric acid and sodium hydroxide for preparing bacterial ghosts from *Listeria*, a gram-positive bacterium, were determined, the minimum time to prepare bacterial ghosts was then determined.

Specifically, a BHI liquid medium was inoculated with *Listeria*, and incubated for 72 hours. After incubation, centrifugation was performed at 10,000 g for 10 minutes to obtain the cultured *Listeria*. The cultured *Listeria* was washed with phosphate-buffered saline (PBS, pH 7.0), and prepared at a concentration of $10^6$ CFU/ml. Thereafter, hydrochloric acid or sodium hydroxide at a concentration of 12.5 mg/ml was mixed with 2 ml of the prepared *Listeria* so that a final concentration became 6.25 mg/ml, followed by incubation at 37° C. *Listeria* was obtained at 15, 30, 45, 60 and 90 minutes after the beginning of culture and the lysis rate was measured. In addition, the colony forming unit (CFU) of *Listeria* was determined by plating in the same manner as described in Example <1-2>. After completion of culture, *Listeria* was harvested, washed twice with PBS, and subjected to centrifugation at 10,000 g for 15 minutes to finally obtain the bacterial ghosts of *Listeria monocytogenes*. Also, in the case of sodium hydroxide treatment, bacteria were harvested at 5, 10, 15, 30, 45 and 60 minutes after the beginning of culture, and whether or not the bacterial ghosts of *Listeria* were prepared was determined.

As a result, as shown in FIG. 3, in the case of groups treated with the MIC of hydrochloric acid, bacterial ghosts were effectively formed within 15 minutes after hydrochloric acid treatment, whereas, when bacterial ghosts prepared from 15 minutes after hydrochloric acid treatment were plated on BHI agar media, colonies were not formed (FIG. 3A). In addition, in the case of groups treated with the MIC of sodium hydroxide, preparation of bacterial ghosts was completed in about 10 minutes after sodium hydroxide treatment, whereas, when bacterial ghosts prepared from 10 minutes after sodium hydroxide treatment were plated on BHI agar media, colonies were not formed (FIG. 3B).

EXAMPLE 2

Identification of Characteristics of *Listeria Monocytogenes* Bacterial Ghosts

<2-1> Determination of Amount of Proteins Remaining in Bacterial Ghosts

To identify the characteristics of the bacterial ghosts of *Listeria* prepared using hydrochloric acid or sodium hydroxide, the amount of proteins remaining in the bacterial ghosts was determined.

Specifically, using the manner described in Example <1-3>, *Listeria* was harvested at 15, 30, 45 and 60 minutes after hydrochloric acid or sodium hydroxide was added, and a denaturation buffer (Laemmli, 1970, Nature 227:680-685) was added thereto, followed by heating for 3 to 5 minutes to prepare denatured samples. The prepared samples were loaded in 12% SDS-PAGE gels, and an SDS-PAGE electrophoresis analysis was performed at a current of 40 mA for 4 hours. After electrophoresis, the gels were stained with a staining solution (containing methanol, acetic acid and water in a volume ratio of 5:1:5) containing Coomassie Brilliant Blue R-250, and the total amount of proteins in bacterial ghosts was determined. SDS-PAGE electrophoresis was performed on *Escherichia coli*, as a non-treated control group, in the same manner to determine the total amount of proteins.

As a result, as shown in FIG. 4, in a group treated with hydrochloric acid, high molecular weight proteins mainly remained in bacterial ghosts, whereas, in a group treated with sodium hydroxide, low molecular weight proteins mainly remained. By comparison of these protein bands with protein bands seen in *Escherichia coli*, as a non-treated control group, it was confirmed that the amount of proteins remaining in the treated groups was small (FIG. 4). From these results, it was confirmed that bacterial ghosts prepared in the present invention lacked proteins present in the cytoplasm and only proteins present in the cell walls required to maintain the structure of the bacterial ghosts remained.

<2-2> Determination of Amount of DNA Remaining in Bacterial Ghosts

After confirming the loss of proteins in the bacterial ghosts of *Listeria monocytogenes* prepared in the present invention, the amount of DNA remaining in the bacterial ghosts was then determined.

Specifically, according to the method of Example <1-3>, *Listeria* was harvested 60 minutes after hydrochloric acid or sodium hydroxide was added, and genomic DNA was extracted using a commercial extraction kit (iNtRON Biotechnology Inc., Korea) according to a protocol provided by the manufacturer. Then, the extracted extracts were loaded in 1% agarose gels containing 0.5 g/ml ethidium bromide (EtBr) and electrophoresis was performed.

In addition, to quantitatively analyze the amount of genomic DNA using real-time PCR, 1 μl of the extracted extracts (1:100 dilution), 1 μl of each forward and reverse primer having nucleotide sequences shown in Table 3 below, 2×SYBR Green II qPCR master mix (Agilent Technology, Inc., USA) and 7 μl distilled water were mixed, and real-time PCR was performed in a Stratagene Mx3000P real-time PCR analyzer under the conditions shown in Table 4 below. In the real-time PCR, genomic DNA was amplified and the amount thereof was quantitatively determined by fluorescence analysis.

*Listeria monocytogenes* bacteria not treated with hydrochloric acid or sodium hydroxide were used as a non-treated control group, *Listeria* treated with a TE buffer solution was used as a solvent control group, and *Listeria* treated with ammonium sulfate was used as a positive control group. Then, real-time PCR analysis was performed using the same method.

TABLE 3

Nucleotide sequences of primers for quantitatively analyzing genomic DNA of *Listeria monocytogenes* bacterial ghosts of the present invention

| Primer name | Sequences |
|---|---|
| Forward primer | 5'-GGAATTCCACGTGTAGCGGTGAAAT-3' |
| Reverse primer | 5'-GACTACCAGGGTATCTAATCCTGTTTG-3' |

The forward and reverse primers were designed to specifically amplify a certain region of 16S rRNA of *Listeria monocytogenes* bacteria.

TABLE 4

Real-time PCR analysis conditions for quantitatively analyzing genomic DNA of *Listeria monocytogenes* bacterial ghosts of the present invention

| Temperature | Time | Repeat (cycle) |
|---|---|---|
| 95° C. | 10 min. | 1 cycle |
| 95° C. | 10 sec. | 40 cycles |
| 55° C. | 10 sec. | |
| 72° C. | 30 sec. | |

As a result, as shown in FIGS. 5 and 6, there was no DNA remaining in bacterial ghosts treated with hydrochloric acid or sodium hydroxide for 60 minutes (FIG. 5). However, when quantitative analysis was performed using real-time PCR, trace amounts of DNA were amplified in the case of sodium hydroxide treatment. This indicates that trace amounts of DNA derived from *Listeria monocytogenes* were present in the bacterial ghosts of a group treated with sodium hydroxide. On the other hand, in the case of hydrochloric acid treatment, DNA amplification was not observed at all and the Ct value was lower than that of a TE buffer solution (FIG. 6). From these results, it was confirmed that bacterial ghosts prepared by treatment with hydrochloric acid or sodium hydroxide according to the present invention did not contain genomic DNA and cytoplasmic proteins and were structures that only retained cell walls. In particular, since the amount of genomic DNA in bacterial ghosts prepared by treatment with hydrochloric acid was significantly less than that in bacterial ghosts prepared by treatment with sodium hydroxide, the bacterial ghosts prepared by treatment with hydrochloric acid are expected to be safer when used as an inactivated vaccine or a foreign antigen carrier.

<2-3> Surface Morphology Analysis of Bacterial Ghosts

To confirm whether bacterial ghosts prepared according to the present invention may be effectively used as an inactivated vaccine or a foreign antigen carrier, surface morphologies of the bacterial ghosts were analyzed using a scanning electron microscope (SEM).

Specifically, according to the method of Example <1-3>, the bacterial ghosts of *Listeria* were obtained 60 minutes after adding hydrochloric acid or sodium hydroxide, suspended in PBS containing 2.5% glutaraldehyde, and fixed at 4° C. for 2 hours, followed by washing with the same solution. Next, bacterial ghosts were transferred into a 1% osmium tetroxide ($OsO_4$) solution, fixed at 4° C. for 1.5 hours, and dehydrated with serially diluted ethanol solutions. The dehydrated bacterial ghosts were dried using liquefied carbon dioxide, coated with gold using a Polaron high-resolution sputter coater to prepare samples, and then the surfaces of the bacterial ghosts were observed using a Hitachi S-4800 FESEM scanning electron microscope. Live *Listeria* bacteria were used as a non-treated control group and the surfaces of the bacteria were observed using SEM by the same method.

As a result, as shown in FIG. 7, when compared with a non-treated control group (image C), in the bacterial ghosts of a hydrochloric acid-treated group, lysis tunnel structures with a definite size were formed in the cell walls (indicated by the arrows) and the morphologies of envelopes had somewhat lysed structures (image). On the other hand, in the bacterial ghosts of a sodium hydroxide-treated group, the size of lysis tunnel structures was slightly small and the morphology of envelopes retained a perfect shape compared with the hydrochloric acid-treated group (image).

Accordingly, the present invention provides bacterial ghosts prepared from gram-positive bacteria by treatment with hydrochloric acid and a method of preparing the same.

According to the present invention, when gram-positive bacteria are cultured after being treated with a minimum inhibitory concentration (MIC) of hydrochloric acid capable of inhibiting colony formation of gram-positive bacteria, bacterial ghosts can be effectively formed. In addition, since the formed bacterial ghosts have no intracellular proteins or DNA while preserving cell wall integrity, the risk of side effects such as secondary infection caused by bacterial growth when the bacterial ghosts are administered to humans is low. Therefore, the bacterial ghosts prepared from gram-positive bacteria according to the method of the present invention can be effectively used as a vaccine or a foreign antigen carrier for preventing or treating gram-positive bacterial infection.

What is claimed is:

1. A method of preparing bacterial ghosts of *Listeria monocytogenes*, the method comprising:

providing *Listeria monocytogenes* as pathogenic bacteria for modification in order to provide a vaccine against a disease caused by *L. monocytogenes;* subjecting *L. monocytogenes* to a treatment with hydrochloric acid for a period of 15 minutes at a concentration of 6.25 mg/ml at a temperature of 37° C. to form bacterial ghosts, which preserve envelopes of the *L. monocytogenes* and antigenic determinants present on the envelopes, whereby there is no DNA remaining in the bacterial ghosts and no live *L. monocytogenes* remaining in the culture; and collecting the bacterial ghosts of *L. monocytogenes* having antigenic determinants present on the envelopes, such that the bacterial ghosts provide the vaccine against the disease caused by *L. monocytogenes.*

* * * * *